United States Patent
McGuckin, Jr. et al.

(10) Patent No.: US 10,390,807 B2
(45) Date of Patent: *Aug. 27, 2019

(54) VASCULAR HOLE CLOSURE DEVICE

(71) Applicant: Rex Medical, L.P., Conshohocken, PA (US)

(72) Inventors: James F. McGuckin, Jr., Radnor, PA (US); John D. Leedle, Chicago, IL (US); James S. Tarmin, Media, PA (US); Thanu Anidharan, Downingtown, PA (US)

(73) Assignee: Rex Medical, L.P., Conshohocken, PA (US)

(*) Notice: Subject to any disclaimer, the term of this patent is extended or adjusted under 35 U.S.C. 154(b) by 501 days.

This patent is subject to a terminal disclaimer.

(21) Appl. No.: 15/089,599

(22) Filed: Apr. 4, 2016

(65) Prior Publication Data

US 2016/0213360 A1 Jul. 28, 2016

Related U.S. Application Data (60) Continuation of application No. 14/616,674, filed on Feb. 7, 2015, now Pat. No. 9,924,930, which is a continuation of application No. 13/290,941, filed on Nov. 7, 2011, now Pat. No. 8,968,361, which is a division of application No. 12/358,411, filed on Jan. 23, 2009, now Pat. No. 8,070,772.

(Continued)

(51) Int. Cl.
*A61B 17/00* (2006.01)

(52) U.S. Cl.
CPC .............................. *A61B 17/0057* (2013.01); *A61B 2017/00004* (2013.01); *A61B 2017/00615* (2013.01); *A61B 2017/00623* (2013.01); *A61B 2017/00659* (2013.01)

(58) Field of Classification Search
CPC ...... A61B 17/0057; A61B 2017/00575; A61B 2017/00606; A61B 2017/00615; A61B 2017/00619; A61B 2017/00628; A61B 2017/00637; A61B 2017/00641; A61B 2017/00654

See application file for complete search history.

(56) References Cited

U.S. PATENT DOCUMENTS 2,024,871 A 12/1935 Parsons
2,398,220 A 4/1946 Gelpcke
(Continued)

FOREIGN PATENT DOCUMENTS

AU 2011244878 5/2012
DE 19604817 8/1997
(Continued)

OTHER PUBLICATIONS

European Search Report Application No. 10175821.7 dated Mar. 17, 2017.

*Primary Examiner* — Dianne Dornbusch
(74) *Attorney, Agent, or Firm* — Neil D. Gershon (57) ABSTRACT

A device for closing an aperture in a vessel wall comprising a covering member having a longitudinal axis and positionable inside the vessel against the internal opening of the aperture and a first spherical retainer positionable external of the vessel. The covering member has a dimension to prevent egress of fluid through the aperture.

18 Claims, 5 Drawing Sheets

Related U.S. Application Data (60) Provisional application No. 61/066,072, filed on Feb. 15, 2008.

(56) References Cited

U.S. PATENT DOCUMENTS

| | | |
|---|---|---|
| 2,413,142 A | 12/1946 | Jones et al. |
| 3,454,004 A | 7/1969 | Leininger et al. |
| 3,467,089 A | 9/1969 | Hasson |
| 3,516,403 A | 6/1970 | Cournut |
| 3,527,223 A | 9/1970 | Shein |
| 3,675,648 A | 7/1972 | Pharriss et al. |
| 3,842,826 A | 10/1974 | Nolan |
| 3,842,827 A | 10/1974 | Jacobs |
| 3,874,388 A | 4/1975 | King et al. |
| 3,913,573 A | 10/1975 | Gutnick |
| 3,937,217 A | 2/1976 | Kosonen |
| 3,958,576 A | 5/1976 | Komiya |
| 3,976,079 A | 8/1976 | Samuels et al. |
| 4,007,743 A | 2/1977 | Blake |
| 4,031,569 A | 6/1977 | Jacob |
| 4,074,668 A | 2/1978 | Indra |
| 4,117,838 A | 10/1978 | Hasson |
| 4,286,497 A | 9/1981 | Shamah |
| 4,317,445 A | 3/1982 | Robinson |
| 4,485,816 A | 12/1984 | Krumme |
| 4,505,274 A | 3/1985 | Speelman |
| 4,512,338 A | 4/1985 | Balko et al. |
| 4,532,926 A | 8/1985 | O'Holla |
| 4,610,671 A | 9/1986 | Luther |
| 4,615,514 A | 10/1986 | Hamlin |
| 4,638,803 A | 1/1987 | Rand |
| 4,665,906 A | 5/1987 | Jervis |
| 4,676,245 A | 6/1987 | Fukuda |
| 4,705,040 A | 11/1987 | Mueller et al. |
| 4,744,364 A | 5/1988 | Kensey |
| 4,796,612 A | 1/1989 | Reese |
| 4,836,204 A | 6/1989 | Landymore et al. |
| 4,890,612 A | 1/1990 | Kensey |
| 4,917,089 A | 4/1990 | Sideris |
| 4,924,866 A | 5/1990 | Yoon |
| 4,971,068 A | 11/1990 | Sahi |
| 5,009,663 A | 4/1991 | Broome |
| 5,021,059 A | 6/1991 | Kensey et al. |
| 5,047,047 A | 9/1991 | Yoon |
| 5,061,274 A | 10/1991 | Kensey |
| 5,108,420 A | 4/1992 | Marks |
| 5,108,421 A | 4/1992 | Fowler |
| 5,123,913 A | 6/1992 | Wilk et al. |
| 5,123,914 A | 6/1992 | Cope |
| 5,171,252 A | 12/1992 | Friedland |
| 5,171,259 A | 12/1992 | Inoue |
| 5,192,300 A | 3/1993 | Fowler |
| 5,192,301 A | 3/1993 | Kamiya et al. |
| 5,192,302 A | 3/1993 | Kensey et al. |
| 5,219,359 A | 6/1993 | McQuilkin et al. |
| 5,222,974 A | 6/1993 | Kensey et al. |
| 5,246,441 A | 9/1993 | Ross et al. |
| 5,269,809 A | 12/1993 | Hayhurst et al. |
| 5,279,572 A | 1/1994 | Hokama |
| 5,282,827 A | 2/1994 | Kensey et al. |
| 5,292,332 A | 3/1994 | Lee |
| 5,306,254 A | 4/1994 | Nash et al. |
| 5,312,435 A | 5/1994 | Nash et al. |
| 5,318,040 A | 6/1994 | Kensey et al. |
| 5,334,210 A | 8/1994 | Gianturco |
| 5,350,399 A | 9/1994 | Erlebacher et al. |
| 5,350,400 A | 9/1994 | Esposito et al. |
| 5,370,661 A | 12/1994 | Branch |
| 5,372,146 A | 12/1994 | Branch |
| 5,385,554 A | 1/1995 | Brimhall |
| RE34,866 E | 2/1995 | Kensey et al. |
| 5,391,183 A | 2/1995 | Janzen et al. |
| 5,409,444 A | 4/1995 | Kensey et al. |
| 5,411,520 A | 5/1995 | Nash et al. |
| 5,433,727 A | 7/1995 | Sideris |
| 5,441,517 A | 8/1995 | Kensey et al. |
| 5,443,481 A | 8/1995 | Lee |
| 5,451,235 A | 9/1995 | Lock et al. |
| 5,474,557 A | 12/1995 | Mai |
| 5,478,352 A | 12/1995 | Fowler |
| 5,478,353 A | 12/1995 | Yoon |
| 5,486,195 A | 1/1996 | Myers et al. |
| 5,507,754 A | 4/1996 | Green et al. |
| 5,520,691 A | 5/1996 | Branch |
| 5,531,759 A | 7/1996 | Kensey et al. |
| 5,540,716 A | 7/1996 | Hlavacek |
| 5,545,178 A | 8/1996 | Kensey et al. |
| 5,549,617 A | 8/1996 | Green et al. |
| 5,549,633 A | 8/1996 | Evans et al. |
| 5,591,204 A | 1/1997 | Janzen et al. |
| 5,593,422 A | 1/1997 | Muijs Van de Moer et al. |
| 5,620,461 A | 4/1997 | Muijs Van De Moer et al. |
| 5,630,833 A | 5/1997 | Katsaros et al. |
| 5,634,936 A | 6/1997 | Linden et al. |
| 5,643,317 A | 7/1997 | Pavcnik et al. |
| 5,649,959 A | 7/1997 | Hannam et al. |
| 5,658,313 A | 8/1997 | Thal |
| 5,662,681 A | 9/1997 | Nash et al. |
| 5,674,231 A | 10/1997 | Green et al. |
| 5,676,689 A | 10/1997 | Kensey et al. |
| 5,690,674 A | 11/1997 | Diaz |
| 5,700,277 A * | 12/1997 | Nash .................. A61B 17/0057 128/887 |
| 5,702,421 A | 12/1997 | Schneidt |
| 5,707,393 A | 1/1998 | Kensey et al. |
| 5,709,707 A | 1/1998 | Lock et al. |
| 5,725,498 A | 3/1998 | Janzen et al. |
| 5,728,132 A | 3/1998 | Van Tassel et al. |
| 5,728,133 A | 3/1998 | Kontos |
| 5,735,875 A | 4/1998 | Bonutti et al. |
| 5,735,877 A | 4/1998 | Pagedas |
| 5,741,223 A | 4/1998 | Janzen |
| 5,741,297 A | 4/1998 | Simon |
| 5,766,206 A | 6/1998 | Wijkamp et al. |
| 5,769,894 A | 6/1998 | Ferragamo |
| 5,782,860 A | 7/1998 | Epstein et al. |
| 5,782,861 A | 7/1998 | Cragg et al. |
| 5,810,845 A | 9/1998 | Yoon |
| 5,810,846 A | 9/1998 | Virnich et al. |
| 5,810,884 A | 9/1998 | Kim |
| 5,814,056 A | 9/1998 | Prosst et al. |
| 5,820,628 A | 10/1998 | Middleman et al. |
| 5,861,003 A | 1/1999 | Latson et al. |
| 5,893,856 A | 4/1999 | Jacob et al. |
| 5,910,155 A | 6/1999 | Ratcliff et al. |
| 5,916,235 A | 6/1999 | Guglielmi |
| 5,916,236 A | 6/1999 | Muijs Van de Moer et al. |
| 5,919,207 A | 7/1999 | Taheri |
| 5,928,266 A | 7/1999 | Kontos |
| 5,964,782 A | 10/1999 | Lafontaine et al. |
| 5,976,159 A | 11/1999 | Bolduc et al. |
| 5,976,174 A | 11/1999 | Ruiz |
| 5,984,933 A | 11/1999 | Yoon |
| 5,984,949 A | 11/1999 | Levin |
| 5,989,268 A | 11/1999 | Pugsley, Jr. et al. |
| 6,001,110 A | 12/1999 | Adams |
| 6,007,563 A | 12/1999 | Nash et al. |
| 6,010,517 A | 1/2000 | Baccaro |
| 6,015,417 A | 1/2000 | Reynolds, Jr. |
| 6,024,756 A | 2/2000 | Huebsch et al. |
| 6,033,427 A | 3/2000 | Lee |
| 6,045,551 A | 4/2000 | Bonutti |
| 6,048,357 A | 4/2000 | Kontos |
| 6,048,358 A | 4/2000 | Barak |
| 6,056,768 A | 5/2000 | Cates et al. |
| 6,063,085 A | 5/2000 | Tay et al. |
| 6,063,106 A | 5/2000 | Gibson |
| 6,066,160 A | 5/2000 | Colvin |
| 6,071,300 A | 6/2000 | Brenneman et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,110,207 A | 8/2000 | Eichhorn et al. |

(56) References Cited

U.S. PATENT DOCUMENTS

| | | | |
|---|---|---|---|
| 6,113,611 A | 9/2000 | Allen et al. |
| 6,117,159 A | 9/2000 | Heubsch et al. |
| 6,117,161 A | 9/2000 | Li et al. |
| 6,120,524 A | 9/2000 | Taheri |
| 6,126,675 A | 10/2000 | Schervinsky et al. |
| 6,136,010 A | 10/2000 | Modesitt et al. |
| 6,139,564 A | 10/2000 | Teoh |
| 6,152,948 A | 11/2000 | Addis |
| 6,162,240 A | 12/2000 | Cates et al. |
| 6,171,320 B1 | 1/2001 | Monassevitch |
| 6,171,329 B1 | 1/2001 | Shaw et al. |
| 6,174,322 B1* | 1/2001 | Schneidt ............ A61B 17/0057 606/213 |
| 6,179,863 B1 | 1/2001 | Kensey et al. |
| 6,197,042 B1 | 3/2001 | Ginn et al. |
| 6,206,893 B1 | 3/2001 | Klein et al. |
| 6,206,907 B1 | 3/2001 | Marino et al. |
| 6,228,096 B1 | 5/2001 | Marchand |
| 6,231,561 B1 | 5/2001 | Frazier et al. |
| 6,231,592 B1 | 5/2001 | Bonutti et al. |
| 6,251,122 B1 | 6/2001 | Tsukernik |
| 6,261,309 B1 | 7/2001 | Urbanski |
| 6,264,673 B1 | 7/2001 | Egnelöv |
| 6,270,515 B1 | 8/2001 | Linden et al. |
| 6,277,140 B2 | 8/2001 | Ginn et al. |
| 6,290,674 B1 | 9/2001 | Roue et al. |
| 6,293,961 B2 | 9/2001 | Schwartz et al. |
| 6,312,446 B1 | 11/2001 | Huebsch et al. |
| 6,315,787 B1 | 11/2001 | Tsugita et al. |
| 6,328,727 B1 | 12/2001 | Frazier et al. |
| 6,334,865 B1 | 1/2002 | Redmond et al. |
| 6,336,914 B1 | 1/2002 | Gillespie, III |
| 6,342,064 B1 | 1/2002 | Koike et al. |
| 6,346,117 B1 | 2/2002 | Greenhalgh |
| 6,348,053 B1 | 2/2002 | Cachia |
| 6,350,270 B1 | 2/2002 | Roue |
| 6,350,274 B1 | 2/2002 | Li |
| 6,355,052 B1 | 3/2002 | Neuss et al. |
| 6,368,341 B1 | 4/2002 | Abrahamson |
| 6,368,343 B1 | 4/2002 | Bonutti et al. |
| 6,391,037 B1 | 5/2002 | Greenhalgh |
| 6,391,048 B1 | 5/2002 | Ginn et al. |
| 6,398,796 B2 | 6/2002 | Levinson |
| 6,409,739 B1 | 6/2002 | Nobles et al. |
| 6,414,664 B1 | 7/2002 | Conover et al. |
| 6,419,669 B1 | 7/2002 | Frazier et al. |
| 6,425,911 B1 | 7/2002 | Akerfeldt et al. |
| 6,436,088 B2 | 8/2002 | Frazier et al. |
| 6,440,152 B1 | 8/2002 | Gainor et al. |
| 6,447,042 B1 | 9/2002 | Jin |
| 6,447,524 B1 | 9/2002 | Knodel et al. |
| 6,451,030 B2 | 9/2002 | Li et al. |
| 6,468,293 B2 | 10/2002 | Bonutti et al. |
| 6,482,179 B1 | 11/2002 | Chu et al. |
| 6,491,714 B1 | 12/2002 | Bennett |
| 6,500,184 B1 | 12/2002 | Chan et al. |
| 6,508,828 B1 | 1/2003 | Akerfeldt et al. |
| 6,537,299 B1 | 3/2003 | Hogendijk et al. |
| 6,547,806 B1 | 4/2003 | Ding |
| 6,569,185 B2 | 5/2003 | Ungs |
| 6,569,187 B1 | 5/2003 | Bonutti et al. |
| 6,503,266 B1 | 7/2003 | Sjögren |
| 6,585,748 B1 | 7/2003 | Jeffree |
| 6,585,750 B2 | 7/2003 | Bonutti et al. |
| 6,596,012 B2 | 7/2003 | Akerfeldt et al. |
| 6,626,930 B1 | 9/2003 | Allen |
| 6,626,937 B1 | 9/2003 | Cox |
| 6,632,238 B2 | 10/2003 | Ginn et al. |
| 6,635,073 B2 | 10/2003 | Bonutti |
| 6,642,169 B2 | 11/2003 | Weatherhead |
| 6,648,903 B1 | 11/2003 | Pierson, III |
| 6,663,653 B2 | 12/2003 | Akerfeldt |
| 6,663,655 B2 | 12/2003 | Ginn |
| 6,676,685 B2 | 1/2004 | Pedros et al. |
| 6,682,489 B2 | 1/2004 | Tenerz et al. |
| 6,699,263 B2 | 3/2004 | Cope |
| 6,712,836 B1 | 3/2004 | Berg et al. |
| 6,712,837 B2 | 3/2004 | Akerfeldt et al. |
| 6,749,621 B2 | 6/2004 | Pantages et al. |
| 6,749,622 B2* | 6/2004 | McGuckin, Jr. ... A61B 17/0057 606/151 |
| 6,764,500 B1 | 7/2004 | Mujis Van De Moer et al. |
| 6,766,186 B1 | 7/2004 | Hoyns et al. |
| 6,786,915 B2 | 9/2004 | Akerfeldt et al. |
| 6,790,220 B2 | 9/2004 | Morris |
| 6,827,727 B2 | 12/2004 | Stalemark et al. |
| 6,846,316 B2 | 1/2005 | Abrams |
| 6,855,153 B2 | 2/2005 | Saadat |
| 6,860,895 B1 | 3/2005 | Akerfeldt et al. |
| 6,863,680 B2 | 3/2005 | Ashby |
| 6,909,130 B2 | 6/2005 | Yoda et al. |
| 6,929,655 B2 | 8/2005 | Egnelöv |
| 6,932,835 B2 | 8/2005 | Bonutti et al. |
| 6,939,363 B2 | 9/2005 | Akerfeldt |
| 6,949,107 B2 | 9/2005 | McGuckin, Jr. et al. |
| 6,960,224 B2 | 11/2005 | Marino et al. |
| 6,972,027 B2 | 12/2005 | Fallin et al. |
| 6,984,219 B2 | 1/2006 | Ashby |
| 6,997,940 B2 | 2/2006 | Bonutti |
| 7,008,440 B2 | 3/2006 | Sing et al. |
| 7,008,442 B2 | 3/2006 | Brightbill |
| 7,025,756 B2 | 4/2006 | Frazier et al. |
| 7,025,776 B1 | 4/2006 | Houser et al. |
| 7,033,380 B2 | 4/2006 | Schwartz et al. |
| 7,033,393 B2 | 4/2006 | Gainor et al. |
| 7,044,916 B2 | 5/2006 | Tenerz et al. |
| 7,048,748 B1 | 5/2006 | Ustuner |
| 7,048,755 B2 | 5/2006 | Bonutti et al. |
| 7,083,635 B2 | 5/2006 | Ginn |
| 7,073,509 B2 | 7/2006 | Tenerz et al. |
| 7,087,073 B2 | 8/2006 | Bonutti |
| 7,094,209 B2 | 8/2006 | Egnelöv |
| 7,115,110 B2 | 10/2006 | Frazier et al. |
| 7,135,032 B2 | 11/2006 | Akerfeldt |
| 7,147,652 B2 | 12/2006 | Bonutti et al. |
| 7,150,757 B2 | 12/2006 | Fallin et al. |
| 7,153,323 B1 | 12/2006 | Teoh et al. |
| 7,169,168 B2 | 1/2007 | Muijs Van de Moer et al. |
| 7,175,648 B2 | 2/2007 | Nakao |
| 7,235,091 B2 | 6/2007 | Thornes |
| 7,267,679 B2 | 9/2007 | McGuckin, Jr. et al. |
| 7,285,097 B2 | 10/2007 | Tenerz |
| 7,288,105 B2 | 10/2007 | Oman et al. |
| 7,316,706 B2 | 1/2008 | Bloom et al. |
| 7,329,270 B2 | 2/2008 | Akerfeldt |
| 7,341,595 B2 | 3/2008 | Hinchliffe et al. |
| 7,361,183 B2 | 4/2008 | Ginn |
| 7,468,068 B2 | 12/2008 | Kolster |
| 7,488,340 B2 | 2/2009 | Kauphusman et al. |
| 7,530,990 B2 | 5/2009 | Perriello et al. |
| 7,566,339 B2 | 7/2009 | Fallin et al. |
| 7,582,105 B2 | 9/2009 | Kolster |
| 7,594,923 B2 | 9/2009 | Fallin et al. |
| 7,597,705 B2 | 10/2009 | Forrsberg et al. |
| 7,618,435 B2 | 11/2009 | Raschdorf, Jr. |
| 7,618,438 B2 | 11/2009 | White et al. |
| 7,621,937 B2 | 11/2009 | Pipenhagen et al. |
| 7,625,352 B1 | 12/2009 | Ashby et al. |
| 7,632,308 B2 | 12/2009 | Loulmet |
| 7,637,921 B2 | 12/2009 | Akerfeldt et al. |
| 7,654,963 B2 | 2/2010 | Egnelöv |
| 7,658,751 B2 | 2/2010 | Stone |
| 7,662,160 B2 | 2/2010 | Bojarski et al. |
| 7,662,161 B2 | 2/2010 | Briganti et al. |
| 7,666,199 B2 | 2/2010 | McIntyre |
| 7,691,112 B2 | 4/2010 | Chanduszko |
| 7,717,929 B2 | 5/2010 | Fallman |
| 7,736,378 B2 | 6/2010 | Maahs et al. |
| 7,749,250 B2 | 7/2010 | Stone et al. |
| 7,758,594 B2 | 7/2010 | Lamson et al. |
| 7,758,611 B2 | 7/2010 | Kato |
| 7,775,988 B2 | 8/2010 | Pijls |
| 7,780,699 B2 | 8/2010 | Zhu |
| 7,824,417 B2 | 11/2010 | Magnusson |

(56) References Cited

U.S. PATENT DOCUMENTS

| | | | |
|---|---|---|---|
| 7,846,180 B2 | 12/2010 | Cerier | |
| 7,862,584 B2 | 1/2011 | Lyons | |
| 7,875,041 B2 | 1/2011 | Mikkaichi et al. | |
| 7,879,072 B2 | 2/2011 | Bonutti et al. | |
| 7,905,904 B2 | 3/2011 | Stone | |
| 7,931,670 B2 | 4/2011 | Fiehler | |
| 7,931,671 B2 | 4/2011 | Tenerz | |
| 7,938,846 B2 | 5/2011 | Akerfeldt | |
| 7,955,340 B2 | 6/2011 | Michlitsch | |
| 7,967,840 B2 | 6/2011 | Chanduszko | |
| 8,007,514 B2 | 8/2011 | Forsberg | |
| 8,016,857 B2 | 9/2011 | Sater | |
| 8,029,534 B2 | 10/2011 | Hruska | |
| 8,070,722 B2 | 12/2011 | Moberg et al. | |
| 8,075,589 B2 | 12/2011 | Pipenhagen et al. | |
| 8,088,143 B2 | 1/2012 | Akerfeldt | |
| 8,105,352 B2 | 1/2012 | Egnelöv | |
| 8,109,968 B2 | 2/2012 | Ashley | |
| 8,118,831 B2 | 2/2012 | Egnelöv | |
| 8,118,832 B1 | 2/2012 | Morris et al. | |
| 8,118,833 B2 | 2/2012 | Seibold | |
| 8,252,005 B2 | 8/2012 | Findlay, III | |
| 8,267,959 B2 | 9/2012 | Fallman | |
| 8,308,758 B2 | 11/2012 | Akerfeldt | |
| 8,308,762 B2 | 11/2012 | Mahlin | |
| 8,348,971 B2 | 1/2013 | Khanna et al. | |
| 8,382,793 B2 | 2/2013 | Egnelöv | |
| 8,398,675 B2 | 3/2013 | Egnelöv | |
| RE44,297 E | 6/2013 | Akerfeldt | |
| 8,469,944 B2 | 6/2013 | Mahlin | |
| 8,480,686 B2 | 7/2013 | Bakos | |
| 8,512,372 B2 | 8/2013 | Egnelov et al. | |
| 8,647,365 B2 | 2/2014 | Tegels | |
| 8,652,166 B2 | 2/2014 | Akerfeldt | |
| 8,663,254 B2 | 3/2014 | Feussner | |
| 8,685,059 B2 | 4/2014 | Walters | |
| 8,734,366 B2 | 5/2014 | Egnelov et al. | |
| 8,870,917 B2 | 10/2014 | Walters | |
| 9,039,738 B2 | 5/2015 | Pipenhagen et al. | |
| 9,486,192 B2 | 11/2016 | Pipenhagen | |
| 2001/0002440 A1 | 5/2001 | Bonutti | |
| 2001/0010005 A1* | 7/2001 | Kammerer | A61B 17/064 606/151 |
| 2002/0055767 A1 | 5/2002 | Forde | |
| 2002/0082622 A1 | 6/2002 | Kane | |
| 2002/0095179 A1 | 7/2002 | Tenerz et al. | |
| 2002/0165561 A1 | 11/2002 | Ainsworth | |
| 2002/0165572 A1 | 11/2002 | Saadat | |
| 2002/0183787 A1 | 12/2002 | Wahr et al. | |
| 2003/0009180 A1 | 1/2003 | Hinchliffe et al. | |
| 2003/0050665 A1 | 3/2003 | Ginn | |
| 2003/0055451 A1 | 3/2003 | Jones et al. | |
| 2003/0088256 A1 | 5/2003 | Conston et al. | |
| 2003/0088269 A1 | 5/2003 | Ashby | |
| 2003/0105487 A1 | 6/2003 | Benz et al. | |
| 2003/0130694 A1 | 7/2003 | Bojarski et al. | |
| 2003/0144695 A1* | 7/2003 | McGuckin, Jr. | A61B 17/0057 606/213 |
| 2003/0187473 A1 | 10/2003 | Berenstein et al. | |
| 2003/0191495 A1 | 10/2003 | Ryan et al. | |
| 2004/0002764 A1 | 1/2004 | Gainor et al. | |
| 2004/0010287 A1 | 1/2004 | Bonutti | |
| 2004/0039413 A1 | 2/2004 | Akerfeldt | |
| 2004/0049207 A1 | 3/2004 | Goldfarb | |
| 2004/0093025 A1 | 5/2004 | Egnelov | |
| 2004/0133236 A1 | 7/2004 | Chanduszko | |
| 2004/0133238 A1 | 7/2004 | Cerier | |
| 2004/0143294 A1 | 7/2004 | Corcoran et al. | |
| 2004/0153103 A1 | 8/2004 | Schwartz et al. | |
| 2004/0158287 A1 | 8/2004 | Cragg et al. | |
| 2004/0176800 A1 | 9/2004 | Paraschac et al. | |
| 2004/0204741 A1 | 10/2004 | Egnelov | |
| 2004/0230223 A1 | 11/2004 | Bonutti et al. | |
| 2005/0033326 A1* | 2/2005 | Briganti | A61B 17/0057 606/151 |
| 2005/0059982 A1 | 3/2005 | Zung et al. | |
| 2005/0065547 A1 | 3/2005 | Marino et al. | |
| 2005/0070957 A1 | 3/2005 | Das | |
| 2005/0075654 A1 | 4/2005 | Kelleher | |
| 2005/0085851 A1 | 4/2005 | Fiehler | |
| 2005/0085852 A1 | 4/2005 | Ditter | |
| 2005/0085855 A1 | 4/2005 | Forsberg | |
| 2005/0090859 A1 | 4/2005 | Ravlkumar | |
| 2005/0096696 A1 | 5/2005 | Forsberg et al. | |
| 2005/0096697 A1 | 5/2005 | Forsberg et al. | |
| 2005/0107807 A1 | 5/2005 | Nakao | |
| 2005/0125030 A1 | 6/2005 | Forsberg et al. | |
| 2005/0125031 A1 | 6/2005 | Pipenhagen et al. | |
| 2005/0125032 A1 | 6/2005 | Whisenant et al. | |
| 2005/0169974 A1 | 8/2005 | Tenerz et al. | |
| 2005/0177182 A1 | 8/2005 | Van der Burg et al. | |
| 2005/0192627 A1 | 9/2005 | Whisenant et al. | |
| 2005/0192630 A1 | 9/2005 | Maas et al. | |
| 2005/0216059 A1 | 9/2005 | Bonutti | |
| 2005/0267524 A1 | 12/2005 | Chanduszko | |
| 2005/0267533 A1 | 12/2005 | Gertner | |
| 2005/0283193 A1 | 12/2005 | Tullber et al. | |
| 2005/0288786 A1 | 12/2005 | Chanduszko | |
| 2006/0069408 A1 | 3/2006 | Kato | |
| 2006/0100665 A1 | 5/2006 | Von Oepen et al. | |
| 2006/0106418 A1 | 5/2006 | Seibold et al. | |
| 2006/0135991 A1 | 6/2006 | Kawaura et al. | |
| 2006/0142797 A1 | 6/2006 | Egnelov | |
| 2006/0155327 A1 | 7/2006 | Briganti | |
| 2006/0167495 A1 | 7/2006 | Bonutti et al. | |
| 2006/0173492 A1 | 8/2006 | Akerfeldt et al. | |
| 2006/0212073 A1 | 9/2006 | Bonutti et al. | |
| 2006/0217760 A1 | 9/2006 | Widomski et al. | |
| 2006/0217765 A1 | 9/2006 | Bonutti et al. | |
| 2006/0229673 A1 | 10/2006 | Forsberg | |
| 2006/0241579 A1 | 10/2006 | Kawaura | |
| 2006/0241695 A1 | 10/2006 | Bonutti et al. | |
| 2006/0265009 A1 | 11/2006 | Bonutti | |
| 2006/0271105 A1 | 11/2006 | Foerster et al. | |
| 2006/0276871 A1 | 12/2006 | Lamson et al. | |
| 2007/0005081 A1 | 1/2007 | Findlay, III | |
| 2007/0010851 A1 | 1/2007 | Chanduszko et al. | |
| 2007/0010857 A1 | 1/2007 | Sugimoto et al. | |
| 2007/0032824 A1 | 2/2007 | Terwey | |
| 2007/0060858 A1 | 3/2007 | Sogard et al. | |
| 2007/0073322 A1 | 3/2007 | Mikkaichi et al. | |
| 2007/0073337 A1 | 3/2007 | Abbott | |
| 2007/0088388 A1 | 4/2007 | Opolski | |
| 2007/0135826 A1 | 6/2007 | Zaver | |
| 2007/0149987 A1 | 6/2007 | Wellman et al. | |
| 2007/0149998 A1 | 6/2007 | Wicks et al. | |
| 2007/0149999 A1 | 6/2007 | Szabo et al. | |
| 2007/0150002 A1 | 6/2007 | Szabo et al. | |
| 2007/0156175 A1 | 7/2007 | Weadock et al. | |
| 2007/0185529 A1 | 8/2007 | Coleman | |
| 2007/0185532 A1 | 8/2007 | Stone et al. | |
| 2007/0198038 A1 | 8/2007 | Cohen | |
| 2007/0239208 A1 | 10/2007 | Crawford | |
| 2007/0239209 A1 | 10/2007 | Fallman | |
| 2007/0244518 A1 | 10/2007 | Callaghan | |
| 2007/0255316 A1 | 11/2007 | McIntyre | |
| 2007/0276437 A1 | 11/2007 | Call | |
| 2008/0065156 A1 | 3/2008 | Hauser | |
| 2008/0071310 A1 | 3/2008 | Hoffman et al. | |
| 2008/0082128 A1 | 4/2008 | Stone et al. | |
| 2008/0114395 A1 | 5/2008 | Mathisen | |
| 2008/0140092 A1 | 6/2008 | Stone et al. | |
| 2008/0243182 A1 | 10/2008 | Bates | |
| 2009/0030450 A1 | 1/2009 | Preinitz et al. | |
| 2009/0036919 A1 | 2/2009 | Preinitz et al. | |
| 2009/0036920 A1 | 2/2009 | Preinitz et al. | |
| 2009/0043333 A1 | 2/2009 | Preinitz et al. | |
| 2009/0076541 A1 | 3/2009 | Chin | |
| 2009/0088778 A1 | 4/2009 | Miyamoto | |
| 2009/0163934 A1 | 6/2009 | Raschdorf, Jr. | |
| 2009/0177225 A1 | 7/2009 | Nunez et al. | |
| 2009/0198256 A1 | 8/2009 | Funamura | |
| 2009/0216266 A1 | 8/2009 | Maruyama et al. | |
| 2009/0216267 A1 | 8/2009 | Williard | |

(56) References Cited

U.S. PATENT DOCUMENTS

| | | |
|---|---|---|
| 2009/0210004 A1 | 9/2009 | McGuckin, Jr. et al. |
| 2009/0234377 A1 | 9/2009 | Mahlin et al. |
| 2009/0248064 A1 | 10/2009 | Preinitz |
| 2009/0326460 A1 | 12/2009 | Beardsley |
| 2010/0114156 A1 | 5/2010 | Mehl |
| 2010/0312224 A1 | 12/2010 | Althoff et al. |
| 2011/0029013 A1 | 2/2011 | McGuckin, Jr. |
| 2011/0071551 A1 | 3/2011 | Singhatat |
| 2011/0082495 A1 | 4/2011 | Ruiz |
| 2011/0270307 A1 | 11/2011 | Szabo |
| 2012/0078294 A1 | 3/2012 | Tarmin et al. |
| 2013/0178895 A1 | 7/2013 | Walters et al. |
| 2014/0025021 A1 | 1/2014 | Walters et al. |

FOREIGN PATENT DOCUMENTS

| | | |
|---|---|---|
| EP | 0637431 | 2/1995 |
| EP | 0920842 | 6/1999 |
| EP | 1671591 | 6/2006 |
| EP | 1671592 | 6/2006 |
| EP | 2055236 | 5/2009 |
| EP | 229486 | 3/2011 |
| EP | 2412317 | 2/2012 |
| WO | 9520916 | 8/1995 |
| WO | WO 95/32670 | 12/1995 |
| WO | 9707741 | 3/1997 |
| WO | 9827868 | 7/1998 |
| WO | 9900055 | 1/1999 |
| WO | 9905977 | 2/1999 |
| WO | 9938454 | 8/1999 |
| WO | WO 01/40348 | 11/2000 |
| WO | WO 2001/021247 | 3/2001 |
| WO | WO 2004/012601 | 2/2004 |
| WO | WO 2004/098418 | 11/2004 |
| WO | WO 0112864 | 12/2004 |
| WO | WO 2006/093970 | 9/2006 |
| WO | WO 2009/108750 | 9/2009 |

\* cited by examiner

FIG_4

FIG_5

FIG_6

VASCULAR HOLE CLOSURE DEVICE

This application is a continuation of application ser. no. 14/616,674, filed Feb. 7, 2015, now U.S. Pat. No. 9,924,530, which is a continuation of application ser. no. 13/290,941, filed Nov. 7, 2011, now U.S. Pat. No. 8,968,361, which is a division of application ser. no. 12/358,411, filed Jan. 23, 2009, now U.S. Pat. No. 8,070,772, which claims priority from provisional application ser. no. 61/066,072, filed Feb. 15, 2008. The entire contents of each of these applications are incorporated herein by reference.

BACKGROUND

Technical Field

This application relates to a vascular device and more particularly to a device for closing openings in vessel walls.

Background of Related Art

During certain types of vascular surgery, catheters are inserted through an incision in the skin and underlying tissue to access the femoral artery in the patient's leg. The catheter is then inserted through the access opening made in the wall of the femoral artery and guided through the artery to the desired site to perform surgical procedures such as angioplasty or plaque removal. After the surgical procedure is completed and the catheter is removed from the patient, the access hole must be closed. This is quite difficult not only because of the high blood flow from the artery, but also because there are many layers of tissue that must be penetrated to reach the femoral artery.

Several approaches to date have been used to close femoral access holes. In one approach, manual compression by hand over the puncture site is augmented by a sandbag or weight until the blood coagulates. With this approach, it can take up to six hours for the vessel hole to close and for the patient to be able to ambulate. This inefficiency increases the surgical procedure time as well as the overall cost of the procedure since the hospital staff must physically maintain pressure and the patient's discharge is delayed because of the inability to ambulate.

In another approach to close the vessel puncture site, a clamp is attached to the operating table and the patient's leg. The clamp applies pressure to the vessel opening. The patient, however, must still be monitored to ensure the blood is coagulating, requiring additional time of the hospital staff and increasing the cost of the procedure.

To avoid the foregoing disadvantages of manual pressure approaches, suturing devices have been developed. One such suturing device, referred to as "the Closer" and sold by Perclose, advances needles adjacent the vessel wall opening and pulls suture material outwardly through the wall adjacent the opening. The surgeon then ties a knot in the suture, closing the opening. One difficulty with the procedure involves the number of steps required by the surgeon to deploy the needles, capture the suture, withdraw the suture, and tie the knot and secure the suture. Moreover, the surgeon cannot easily visualize the suture because of the depth of the femoral artery (relative to the skin) and essentially ties the suture knot blindly or blindly slips a pre-tied knot into position. Additionally, the ability to tie the knot varies among surgeons; therefore success and accuracy of the hole closure can be dependent on the skill of the surgeon. Yet another disadvantage of this suturing instrument is that the vessel opening is widened for insertion of the instrument, thus creating a bigger opening to close in the case of failure to deliver the closure system. It is also difficult to pass the needle through calcified vessels.

U.S. Pat. No. 4,744,364 discloses another approach for sealing a vessel puncture in the form of a device having an expandable closure member with a filament for pulling it against the vessel wall. The closure member is held in place by a strip of tape placed on the skin to hold the filament in place. However, the closure device is still subject to movement which can cause leakage through the puncture. Additionally, if the suture becomes loose, the closure member is not retained and can flow downstream in the vessel. Moreover, since the suture extends through the skin, a potential pathway for infection is created. The closure device in U.S. Pat. No. 5,545,178 includes a resorbable collagen foam plug located within the puncture tract. However, since coagulation typically takes up to twenty minutes and blood can leak in between the plug and tissue tract, manual pressure must be applied to the puncture for a period of time, until the collagen plug expands within the tract.

It would therefore be advantageous to provide a device which would more quickly and effectively close openings (punctures) in vessel walls. Such device would advantageously avoid the aforementioned time and expense of applying manual pressure to the opening, simplify the steps required to close the opening, avoid widening of the opening, and more effectively retain the closure device in the vessel.

Commonly assigned co-pending patent application Ser. No. 10/847,141, filed May 17, 2004, discloses effective vascular hole closure devices which have the foregoing advantages. It would be further advantageous to provide a vascular hole closure device which is adjustable to accommodate different tissue thicknesses and applies a more constant clamping/retaining force between the intravascular and extravascular components of the device irrespective of tissue thickness.

SUMMARY

The present invention overcomes the disadvantages and deficiencies of the prior art. The present invention provides a device for closing an aperture in a vessel wall, the aperture having an external opening in an external region of the vessel wall and an internal opening in an internal region of the vessel wall. The device comprises a covering member having a longitudinal axis and positionable inside the vessel against the internal opening of the aperture and a first spherical retainer positionable external of the vessel. The covering member has a dimension to prevent egress of fluid through the aperture.

The device preferably includes a second spherical member and first and second sutures attached to respective spherical members. Preferably, pulling of the first suture moves the first retainer toward the covering member and pulling of the second suture moves the second retainer toward the covering member.

Preferably the covering member is composed of a resorbable material. In a preferred embodiment, the retainers and sutures are also composed of a resorbable material.

In a preferred embodiment, the retainers in a placement position are positioned in a substantially side by side relationship and in the delivery position are positioned in stacked relationship.

The present invention also provides a method of closing an aperture in a vessel wall, the aperture having an external opening in an external region of the vessel wall and an internal opening in an internal region of the vessel wall. The method comprises inserting a covering member inside the vessel against the internal opening of the aperture, the covering member having a dimension to prevent egress of fluid through the aperture, inserting a first spherical retainer external of the vessel, and advancing the first retainer toward the covering member.

Preferably, the step of advancing the first retainer comprises the step of moving a suture, wherein the first retainer is fixedly attached to the suture. The method also preferably includes the step of inserting a second spherical retainer external of the vessel and advancing the second retainer toward the covering member by suture movement. Preferably, the first and second retainers are placed in side by side relationship and left in the body to resorb over a period of time.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Figure 1:
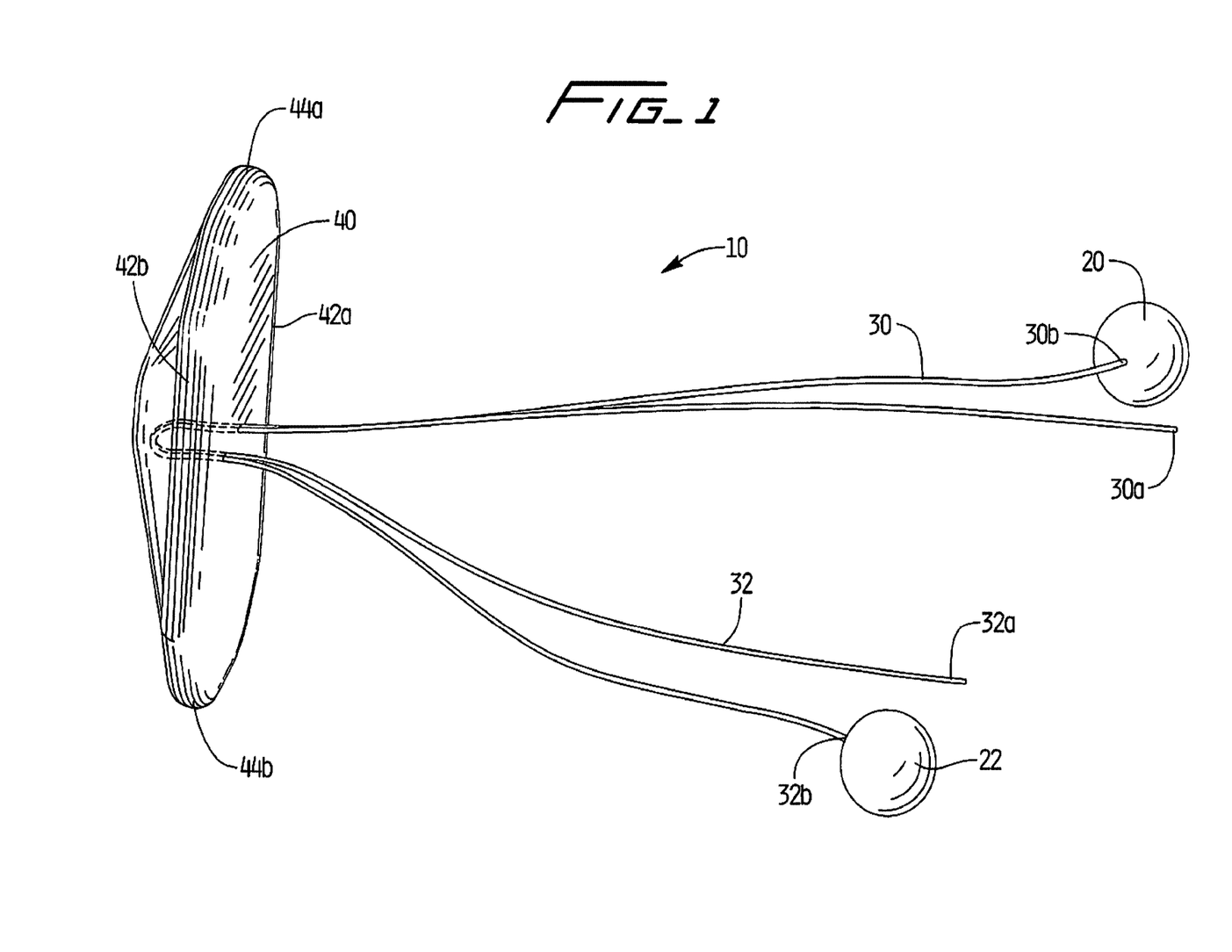
FIG. 1 is a perspective view of a first embodiment of the closure device of the present invention.

Referring now in detail to the drawings where like reference numerals identify similar or like components throughout the several views, FIG. 1 is a perspective view of a first embodiment of the vascular hole (aperture) closure device of the present invention. The device is intended to close an aperture in the vessel wall, typically formed after removal of a catheter previously inserted through the vessel wall into the vessel lumen for performing angioplasty or other interventional procedures. The aperture extends through the patient's skin and underlying tissue, through the external wall of the vessel, through the wall of the vessel, and through the internal wall of the vessel to communicate with the internal lumen of the vessel. The closure device of the present invention has an intravascular component to block blood flow and an extravascular component to retain the intravascular component.

More specifically, the closure device includes a covering member or patch positioned within the vessel against the internal wall of the vessel to block blood flow and two spherical retainers positioned external of the vessel wall to retain the covering member in its blocking position. Each retainer is fixedly attached to a suture such that pulling of the suture advances the attached retainer toward the covering member to ultimately position the retainers in a side by side relationship either against or adjacent the external surface of the vessel wall.

Turning to FIGS. 1-7, a first embodiment of the closure device of the present invention is illustrated. Hole (aperture) closure device 10 has a covering member or patch 40 and a first spherical retainer or ball 20 and a second spherical retainer or ball 22. The covering member 40 is dimensioned and configured for positioning inside the vessel on the internal side of the vessel aperture against the internal wall of the vessel; the retainers 20, 22 are configured to be positioned outside the vessel wall adjacent or contiguous the external side of the vessel aperture.

Covering member 40, preferably elongated in configuration as shown, is retained in a delivery sheath in a longitudinal position for delivery to the vessel, and then pivots to a transverse position within the vessel lumen (substantially perpendicular to an axis extending through the aperture), for orientation to cover (patch) the vessel aperture on the internal side. This movement is illustrated in FIGS. 37A-37D of commonly assigned co-pending patent application Ser. No. 10/847,141, filed May 17, 2004, the entire contents of which are incorporated herein by reference (hereinafter the '141 application).

The spherical retainers are preferably held in the delivery tube in a stacked relationship (not shown), with retainer 22 atop retainer 20 (or vice versa).

Figure 4:
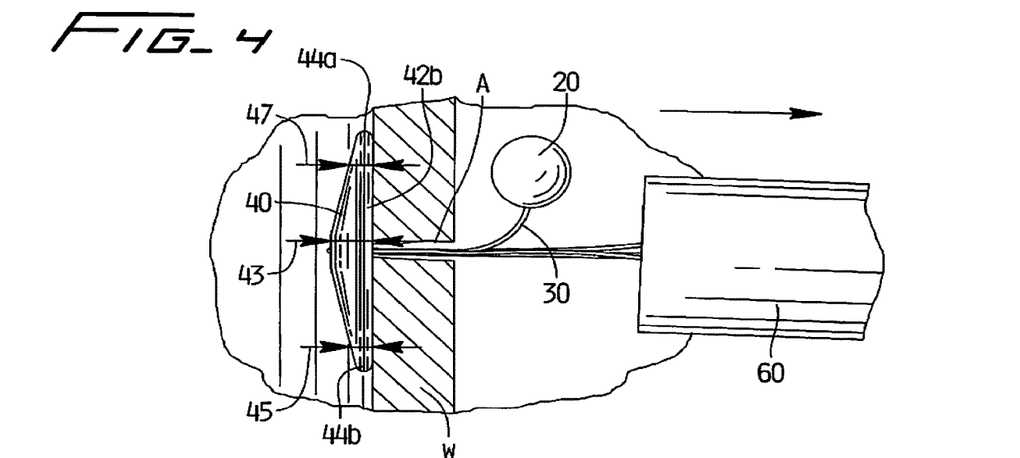
FIG. 4 is a side view illustrating one of the spherical retainers of the closure device deployed from the sheath (the vessel wall shown in cross-section)
Figure 5:
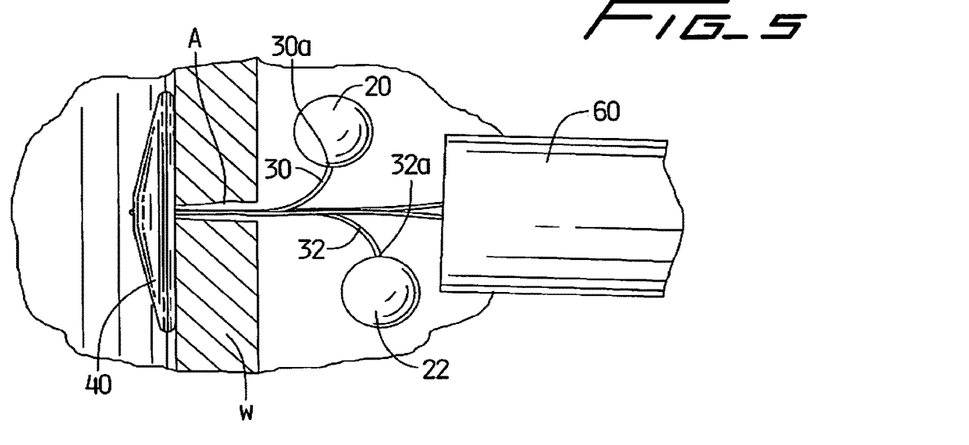
FIG. 5 illustrates both spherical retainers deployed from the sheath.

The elongated covering member 40 functions to cover (patch) the internal opening in the vessel wall to prevent the egress of blood. With reference to FIGS. 1 and 4, the covering member 40 is preferably somewhat oval shaped with elongated substantially parallel side walls 42a, 42b and end walls 44a, 44b connecting the side walls 42a, 42b. Other shapes of the covering member are also contemplated. Although the ends preferably have substantially straight wall portions 44a, 44b, curved walls are also contemplated. Covering member preferably has a thicker region 43 in the central region than the first and second end regions 45, 47. Other dimensions are also contemplated.

The longitudinal axis of covering member 40 defines a lengthwise dimension and transverse axes define a shorter widthwise dimensions. The widthwise dimension of the covering member 40 can be about 2.5 mm (for a 6 Fr device). In a preferred embodiment, the covering member 40 is about 3.3 mm in widthwise dimension. Other dimensions are also contemplated. The width preferably is at least substantially equal to the dimension of the internal opening in the vessel wall to effectively cover the opening. In a preferred embodiment, the covering member 40 has a length of about 8 mm (in a 6 French system).

It should be appreciated that alternatively the covering member could be provided with an enlarged width region as illustrated in the embodiment of FIG. 1 of the '141 application.

The covering member could also be configured asymmetrically so that the enlarged region is off-centered to accommodate widening of the aperture as the member is pulled at an angle. The covering member could also be configured in a paddle shaped with a narrowed region adjacent a wider region as in FIGS. 9B-9E of the '141 application. Other covering member configurations including those disclosed in the '141 application could be utilized with the retainers of this present application.

The elongated covering member can be composed of materials such as polycarbonate or polyurethane. Preferably it is composed of resorbable materials such as lactide/ glycolide copolymers that after a period of time resorb in the body. If composed of resorbable material, the covering member could optionally have regions of varying resorbability. Varying degrees of resorbability can be achieved for example by utilizing different materials having differing resorbable characteristics or by varying the mass of the covering member (increased mass increases resorbtion time).

Spherical retainers 20 and 22 are preferably composed of resorbable material. In a preferred embodiment, the diameter of each retainer 20, 22 is about 0.095 inches, although other dimensions are contemplated. Although shown as spheres, other rounded shapes are also contemplated. The retainers could alternatively be made of non-absorbable polymeric or metallic material.

When the retainers 20 and 22 are released from the delivery instrument, they are spaced further from the covering member 40. They are then configured to be advanced toward the covering member 40. More specifically, each retainer 20, 22 is fixedly secured to a respective suture 30, 32. Sutures 30, 32 are preferably made of polymeric material and are preferably resorbable, composed of a material such as polydioxanome. It is also contemplated that alternatively a metallic material could be utilized.

As shown, suture 30 has a free end 30*a* and an opposite end 30*b* secured to retainer 20 by molding, gluing, forming a knot, or other methods. Similarly, suture 32 has a free end 32*a* and an opposite end 32*b* secured to retainer 22 in a similar manner. The suture is shown in the embodiment of FIG. 1 looped through the covering member. Other methods of attachment are also contemplated. For example, in the alternative embodiment of FIG. 8, sutures 150, 152 are attached to covering member 140 by a loop of suture 160. Loop 160 extends upwardly (proximally) from the covering member 140 and the sutures 150, 152 are looped through suture loop 160.

To advance the retainers 20, 22 toward the vessel wall (and covering member), the free end of each suture is pulled proximally (in a direction of the arrow of FIG. 4, thereby moving the respective retainer in the opposite direction closer to the aperture A and vessel wall W. Once tightened against the tissue, a sufficient retention force is maintained, i.e. a proximal pulling force on the covering member 40 to pull it slightly upwardly (proximally) against the vessel wall. The retainers 20, 22 therefore help to prevent the covering member 40 from separating from the vessel wall (e.g. moving in the direction toward the opposing vessel wall) which could create an unwanted gap between the covering member 40 and the vessel opening to allow blood flow. The extent to which the retainers 20, 22 move toward the wall (and thus their distance from the vessel wall in their final placement position) will depend on the tissue thickness. Thus, the closure device can adjust for different tissue thicknesses and apply a constant retention force regardless of tissue thickness.

The delivery instrument for inserting the closure device extends through an opening in the skin, through the tissue tract to the vessel, through an external opening in the vessel wall, through the aperture in the vessel wall, and through an internal opening on the internal side of the vessel wall into the vessel lumen.

Figure 2:
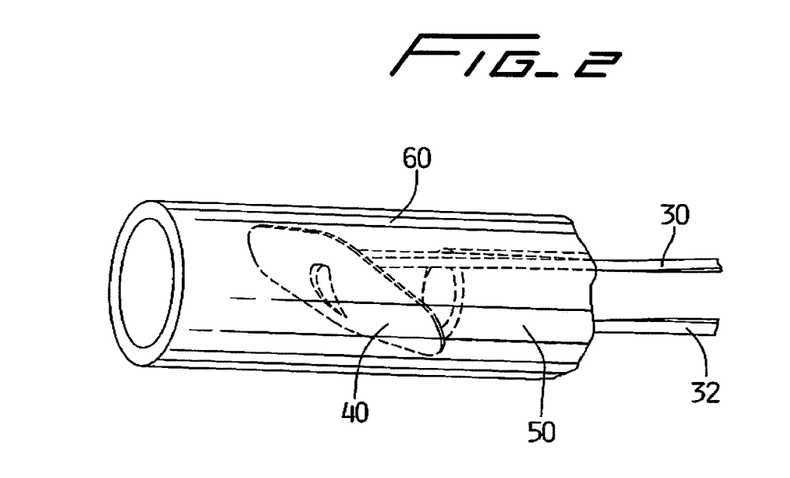
FIG. 2 is a side perspective view of the covering member of the closure device of FIG. 1 shown within the delivery sheath.
Figure 3:
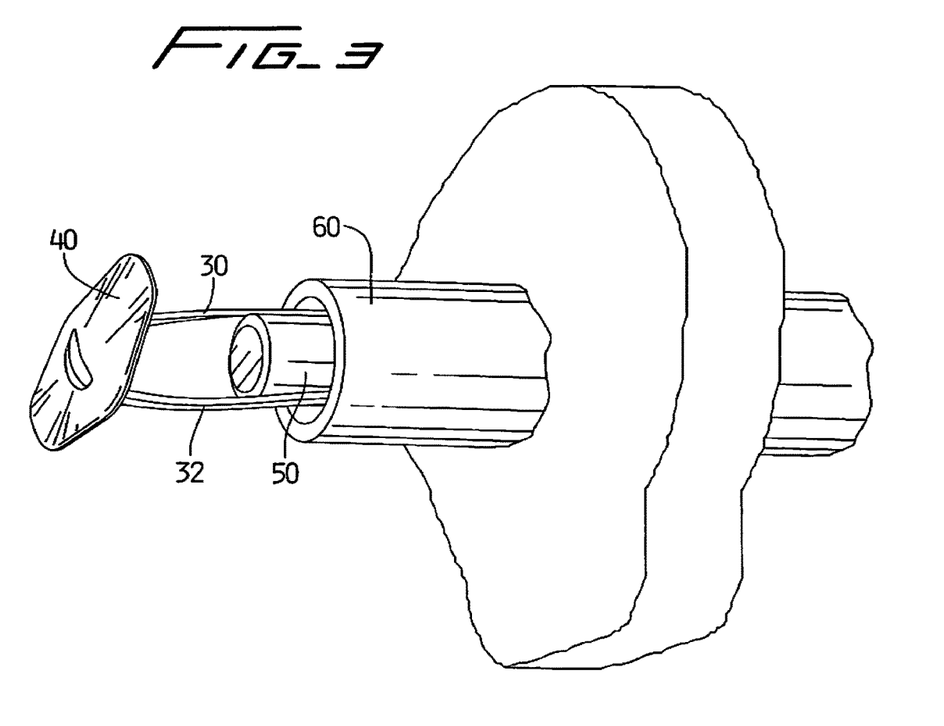
FIG. 3 is a side perspective view illustrating the covering member of FIG. 2 deployed from the delivery sheath.

The covering member 40 in FIG. 2 is outside retainer tube 50 and within delivery sheath 60 in a tilted position. The covering member 40 emerges from the sheath 60 and moves from a tilted and preferably a somewhat straightened positioned, (substantially aligned with the longitudinal axis of the sheath) to a transverse position within the vessel (see FIG. 3). (Note the vessel wall is shown in FIG. 3 but the rest of the vessel and tissue are removed for clarity.) The retainers 20, 22 remain within tube 50. Note the covering member 40 can be ejected by a pusher (not shown) contacting the side or top wall.

As shown in FIG. 4 covering member 40 is pulled proximally to abut the internal opening on the internal side of the vessel W to cover (patch) the opening and the suture extends through the opening A in the vessel wall. The first retainer 20 is shown ejected from the sheath S in FIG. 4 either by advancing the retainer, retracting the sheath or relative movement of both. The second retainer 22 is still within tube 50. The second retainer 22 is then deployed in a similar manner as retainer 20 and is shown outside sheath 60 in FIG. 5. Note that in the delivery position, the retainers 20 and 22 are preferably in a stacked relationship (not shown) to minimize the transverse dimension of the delivery system.

Figure 6:
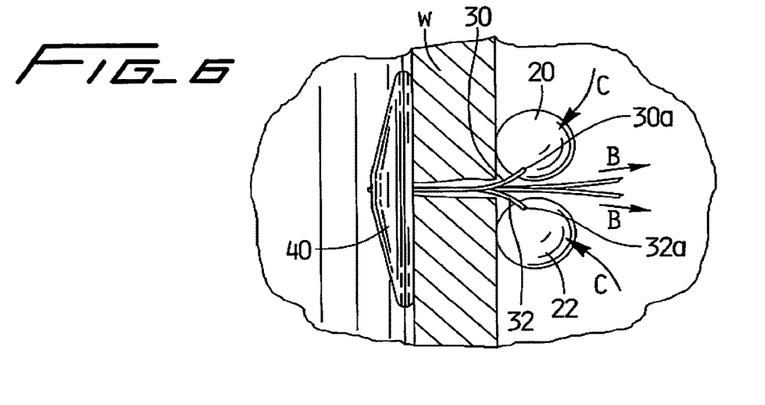
FIG. 6 illustrates the sutures pulled to move the spherical retainers toward the covering member for positioning in a side by side relationship against the outer surface of the vessel wall.

Then, to retain the covering member 40 in position against the vessel wall to block blood flow therethrough, sutures 30 and 32 are pulled proximally from their free ends in the direction of arrows B of FIG. 6, thereby advancing the retainers 20, 22 distally in the direction of arrows C toward the vessel wall V and covering member 40. As shown, the retainers 20, 22 can be moved to a position contiguous to the vessel wall, or depending on tissue thickness, may be adjacent the wall with some tissue interposed between the retainers and vessel wall. The retainers 20, 22 in this position apply a proximal (upward) force on the elongated covering member 40 to limit movement of the covering member into the vessel. The retainers in this placement position are preferably in a substantially side by side relationship as shown in FIG. 7.

Figures 7, 8:
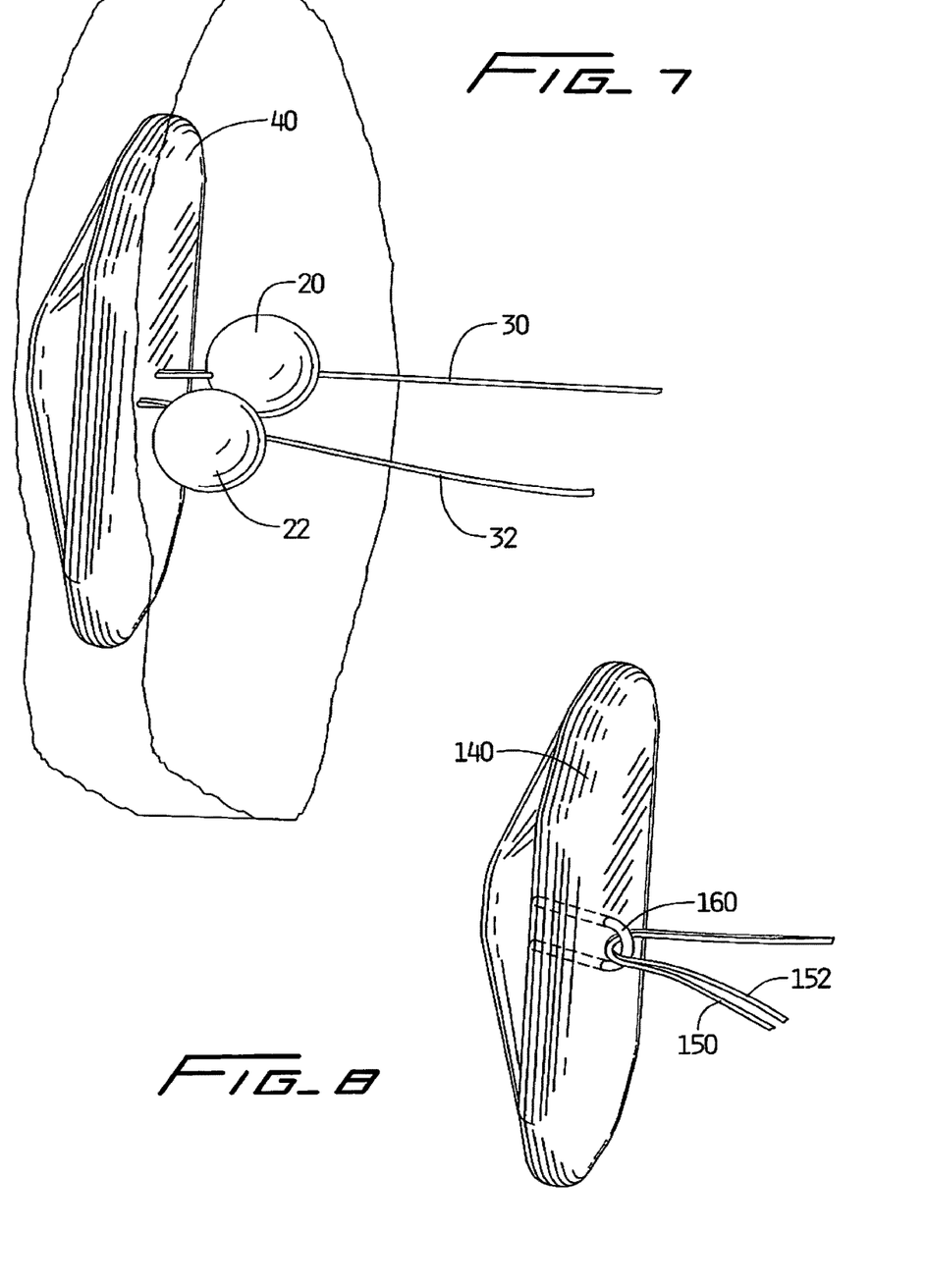
FIG. 7 is a perspective view illustrating the retainers in the placement position.
FIG. 8 is a perspective view of the covering member and sutures of an alternate embodiment of the closure device of the present invention showing the sutures attached to the covering member via a looped suture.
Figure 9:
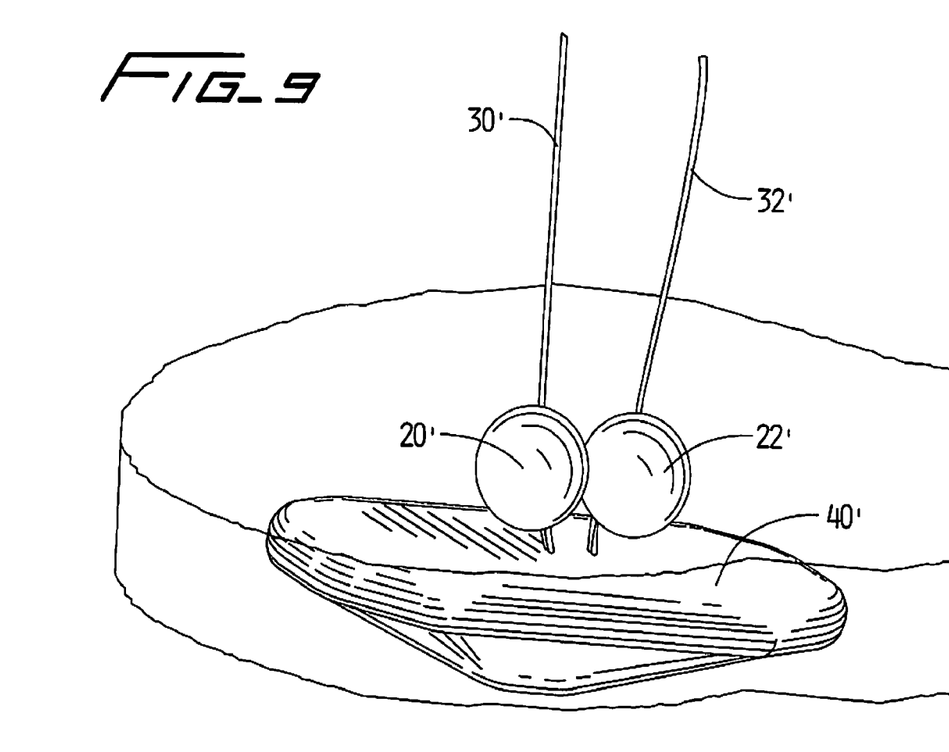
FIG. 9 is a perspective view illustrating an alternate orientation of the retainers in the placement position.

As shown in FIG. 7, in the side by side relationship, the retainers 20 and 22 are alongside in a transverse orientation with respect to covering member 40. That is, they are positioned along the width of the covering member 40. However it is also contemplated that the retainers in the placement position can be in a lengthwise orientation (substantially parallel to the longitudinal axis of the covering member) as shown in FIG. 9 where corresponding components to FIG. 7 have prime designations. The retainers could also be in other side by side arrangements at angles to the longitudinal axis.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A vascular device for closing an aperture in a wall of a vessel, the vascular device comprising:
   an intravascular distal covering member positionable inside the vessel, the covering member having a length and a width, the covering member pivoting from a first position to a second placement position when outside a delivery device;
   an extravascular first retainer positionable external of the vessel, the first retainer positioned proximal of the covering member during delivery and placement outside of the aperture; and
   a first flexible member extending between the distal covering member and the first retainer, wherein applying a proximally directed force on a portion of the first flexible member advances the first retainer distally toward the covering member as the position of the first retainer remains fixed with respect to a first end and a second end of the first flexible member.

2. The device of claim 1, further comprising a second retainer positionable proximal of the covering member and external of the vessel, the second retainer movable distally toward the covering member.

3. The device of claim 2, further comprising a second flexible member extending between the distal covering member and the second retainer, wherein applying a proximally directed force on a portion of the second flexible member advances the second retainer distally toward the covering member, wherein the second retainer is advanceable independently of the first retainer and after the first retainer is advanced.

4. The device of claim 3, wherein the covering member, first flexible member, first retainer, second flexible member and second retainer are composed of a resorbable material.

5. The device of claim 2, wherein the first and second retainers in a placement position are positioned in a substantially side by side relationship.

6. The device of claim 1, wherein the covering member, first flexible member and first retainer are composed of a resorbable material.

7. The device of claim 1, wherein the length of the covering member is greater than the width of the covering member.

8. The device of claim 7, wherein the covering member has a first end region, a second end region and an intermediate region between the first and second end regions, and the intermediate region is thicker than the first and second end regions.

9. A vascular device for closing an aperture in a wall of a vessel, the aperture extending through the wall of the vessel from a first proximal end to a second distal end opposite the first end and communicating with an internal lumen of the vessel, the vascular device comprising:
an intravascular distal covering member, the covering member having a dimension to prevent blood flow through the aperture, the covering member positionable within the lumen of the vessel and against an internal side of the aperture, the covering member having a longitudinal axis, and a first end region at a first end of the longitudinal axis and a second end region at a second opposite end of the longitudinal axis;
an extravascular first retainer having a width and positionable external of the vessel in a placement position, the first retainer in the placement position being outside the aperture, the first retainer positioned proximal of the covering member during delivery and placement and movable distally toward the covering member;
a first flexible member extending from the distal covering member to the first retainer and attached to the first retainer to effect movement thereof, the first flexible member extending though the aperture, the width of the first retainer being greater than a width of the first flexible member;
an extravascular second retainer having a width and positionable external of the vessel in a placement position, the second retainer in the placement position being outside the aperture, the second retainer positioned proximal of the covering member during delivery and placement and movable distally toward the covering member; and
a second flexible member extending from the distal covering member to the second retainer and attached to the second retainer to effect movement thereof, the width of the second retainer being greater than a width of the second flexible member, the first and second flexible members extending though the aperture and being the only components of the vascular device extending through the aperture.

10. The device of claim 9, wherein the covering member and the first and second retainers are composed of a resorbable material.

11. The device of claim 10, wherein the first and second retainers in a placement position are not positioned atop one another but are positioned side by side such that the first retainer is closer to the first end region of the covering member and the second retainer is closer to the second end region of the covering member.

12. A vascular hole closure system for closing an aperture in a vessel comprising:
a delivery device having a distal opening at a distal end;
an intravascular distal covering member, the covering member moving from a first position to a second placement position when outside the distal opening of the delivery device;
an extravascular first retainer positionable external of the vessel, the first retainer positioned proximal of the covering member during delivery and placement, the first retainer contained within the delivery device during insertion of the delivery device into the vessel to deliver the covering member inside the vessel; and
an extravascular second retainer positionable external of the vessel, the second retainer positioned proximal of the covering member during delivery and placement, the second retainer contained within the delivery device during insertion of the delivery device into the vessel to deliver the covering member inside the vessel, wherein the first retainer is advanceable from a first position within the delivery device to a second position outside the distal opening of the delivery device and the second retainer is advanceable from a first position within the delivery device to a second position outside the distal opening of the delivery device subsequent to advancement of the first retainer to the second position outside the distal opening of the delivery device, the first and second retainers applying a retention force in the second position to maintain the covering member, and the first and second retainers are advanced by separate members attached thereto.

13. The device of claim 12, wherein the covering member and the first and second retainers are composed of a resorbable material.

14. The device of claim 12, wherein the first and second retainers in a placement position are positioned side by side such that the first retainer is closer to a first end region of the covering member and the second retainer is closer to the second opposite end region of the covering member, the first end region being adjacent a first end of a longitudinal axis of the covering member and the second end region being adjacent a second end of the longitudinal axis of the covering member.

15. The system of claim 14, wherein the covering member has a central region between the first and second end regions, and the central region is thicker than the first and second end regions.

16. The system of claim 12, wherein a length of the covering member is greater than a width of the covering member.

17. The system of claim 12, wherein the covering member pivots from a first position to a transverse position when delivered from the delivery device.

18. The system of claim 12, wherein a pusher contacts the covering member to advance the covering member from the delivery device.

\* \* \* \* \*